United States Patent
Zhu et al.

(10) Patent No.: US 11,172,903 B2
(45) Date of Patent: Nov. 16, 2021

(54) SYSTEMS AND METHODS FOR DETERMINING KINETIC PARAMETERS IN DYNAMIC POSITRON EMISSION TOMOGRAPHY IMAGING

(71) Applicant: UIH AMERICA, INC., Houston, TX (US)

(72) Inventors: Wentao Zhu, Houston, TX (US); Hongdi Li, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 333 days.

(21) Appl. No.: 16/052,366

(22) Filed: Aug. 1, 2018

(65) Prior Publication Data

US 2020/0037975 A1     Feb. 6, 2020

(51) Int. Cl.
*A61B 6/00*    (2006.01)
*A61B 6/03*    (2006.01)
*G06T 11/00*   (2006.01)

(52) U.S. Cl.
CPC ............ *A61B 6/5217* (2013.01); *A61B 6/037* (2013.01); *A61B 6/507* (2013.01); *G06T 11/006* (2013.01); *G06T 2210/41* (2013.01)

(58) Field of Classification Search
CPC ........... A61B 6/037; A61B 6/12; A61B 6/507; A61B 6/5217; G06T 11/006; G06T 2210/41; G16H 50/30
See application file for complete search history.

(56) References Cited

U.S. PATENT DOCUMENTS

| 8,831,323 B2 | 9/2014 | Kelly et al. |
| 2008/0230703 A1 | 9/2008 | Kadrmas et al. |
| 2010/0054559 A1 | 3/2010 | Narayanan |
| 2010/0296714 A1* | 11/2010 | Schmainda ........ G01R 33/5601 382/131 |
| 2014/0248210 A1 | 9/2014 | Bradbury et al. |
| 2015/0363948 A1 | 12/2015 | Leahy et al. |

(Continued)

OTHER PUBLICATIONS

Angelis G. et al., Convergence Optimization of Parametric MLEM Reconstruction for Estimation of Patlak Plot Parameters, Computerized Medical Imaging and Graphics, 35:407-416, 2011.

(Continued)

*Primary Examiner* — Joanne M Hoffman
*Assistant Examiner* — Alexei Bykhovski
(74) *Attorney, Agent, or Firm* — Metis IP LLC

(57) ABSTRACT

A method for imaging may include directing a PET scanner to perform scans of a subject injected with a tracer during a first time period. The method may also include generating PET images by reconstructing the PET data that are generated by the PET scanner based on the scans of the subject. The method may also include determining a first portion of a blood input function of the tracer in the subject based on the PET images. The method may also include determining an integral of a second portion of the blood input function based on a kinetic model, the PET data, and the first portion of the blood input function. The method may also include determining kinetic parameters of the kinetic model based on the PET data, the first portion of the blood input function, and the integral of the second portion of the blood input function.

20 Claims, 7 Drawing Sheets

(56) References Cited

U.S. PATENT DOCUMENTS

2018/0369611 A1* 12/2018 Owens ................ A61N 5/1049
2019/0057506 A1   2/2019 Long et al.

OTHER PUBLICATIONS

Sha W., Quantitative Analysis of Biological Effects on 18F-FDG Uptake in Tumors: from In-vitro to In-vivo Studies, UCLA Electronic Theses and Dissertations, 2012, 143 pages.
International Search Report in PCT/US2019/44574 dated Nov. 5, 2019, 2 pages.
Written Opinion in PCT/US2019/44574 dated Nov. 5, 2019, 7 pages.

* cited by examiner

SYSTEMS AND METHODS FOR DETERMINING KINETIC PARAMETERS IN DYNAMIC POSITRON EMISSION TOMOGRAPHY IMAGING

TECHNICAL FIELD

The present disclosure generally relates to systems and methods for imaging, and more specifically, relates to systems and methods for determining kinetic parameters in dynamic positron emission tomography (PET) imaging.

BACKGROUND

PET imaging has been widely used in clinical examination and disease diagnosis in recent years. PET imaging may include static PET imaging and Dynamic PET imaging. In contrast with static PET imaging, dynamic PET imaging may provide a set of images over a dynamic scan time, and dynamic PET data may also provide rich information related to physiological parameters (e.g., perfusion pressure) that indicate the functional status of the imaged tissue. Kinetic compartmental models (or "kinetic models" for brevity) may be used to describe the exchange of tracer between different compartments by kinetic parameters during dynamic PET imaging. The estimation of the kinetic parameters is of significance in clinical examination and disease diagnosis. A blood input function (also referred to as an arterial input function or an arterial time-activity curve (TAC)) may be a key input into a kinetic model for estimating the kinetic parameters. In existing processes, the blood input function may be obtained by blood sampling or image analysis. The blood sampling may include sampling a certain amount of arterial blood of a subject (e.g., a patient) injected with the tracer at a plurality of time points, so as to determine the arterial TAC of the tracer. The image analysis may include reconstructing a set of PET images over time and fitting the arterial TAC of the tracer based on the set of PET images. In order to obtain the entire arterial TAC of the tracer, when the tracer is injected into the subject, the scan of the subject may start at the same time. As a result, the blood sampling and the image analysis for obtaining the blood input function may be time-consuming and costly. Therefore, it is desirable to provide systems and methods for determining kinetic parameters of dynamic PET imaging with improved efficiency.

SUMMARY

According to a first aspect of the present disclosure, a system for imaging may include a positron emission tomography (PET) scanner, one or more storage devices, and one or more processors configured to communicate with the one or more storage devices. The PET scanner may perform scans of a subject injected with a tracer during a first time period. The tracer may be injected into the subject at an injection time prior to the first time period. The PET scanner may generate PET data based on the scans of the subject. The one or more storage devices may include a set of instructions. When the one or more processors executing the set of instructions, the one or more processors may be directed to perform one or more of the following operations. The one or more processors may generate PET images based on the scans of the subject by reconstructing the PET data. The one or more processors may determine a first portion of a blood input function of the tracer in the subject based on the PET images. The first portion of the blood input function may be associated with the first time period. The one or more processors may determine an integral of a second portion of the blood input function based on a kinetic model, the PET data, and the first portion of the blood input function. The second portion of the blood input function may be associated with a second time period between the injection time and a start time of the first time period. The one or more processors may determine kinetic parameters of the kinetic model based on the PET data, the first portion of the blood input function, and the integral of the second portion of the blood input function. The kinetic parameters may indicate a metabolism of the tracer in the subject.

In some embodiments, the one or more processors may determine whether there is a lesion in the subject based on the kinetic parameters.

In some embodiments, to determine the integral of the second portion of the blood input function based on the kinetic model, the PET data, and the first portion of the blood input function, the one or more processors may determine a Patlak estimation based on the kinetic model. The one or more processors may determine the integral of the second portion of the blood input function based on the Patlak estimation, the PET data, and the first portion of the blood input function.

In some embodiments, the integral of the second portion of the blood input function may be determined based on a least squares (LS) algorithm.

In some embodiments, the integral of the second portion of the blood input function may be determined based on an expectation maximization (EM) algorithm.

In some embodiments, the tracer may be applicable to a two-tissue compartment model.

In some embodiments, the tracer may be an irreversible tracer.

In some embodiments, the start time of the first time period may be equal to a time point at which the distribution of the tracer in the subject is deemed to have reached a steady state.

In some embodiments, the start time of the first time period may be after a time point at which the distribution of the tracer in the subject is deemed to have reached a steady state.

In some embodiments, the PET scanner may perform the scans of the subject at a single bed position or at multiple bed positions.

According to another aspect of the present disclosure, a method for imaging may include one or more of the following operations. One or more processors may direct a positron emission tomography (PET) scanner to perform scans of a subject injected with a tracer during a first time period. The tracer may be injected into the subject at an injection time prior to the first time period. The one or more processors may generate PET images by reconstructing the PET data that are generated by the PET scanner based on the scans of the subject. The one or more processors may determine a first portion of a blood input function of the tracer in the subject based on the PET images. The first portion of the blood input function may be associated with the first time period. The one or more processors may determine an integral of a second portion of the blood input function based on a kinetic model, the PET data, and the first portion of the blood input function. The second portion of the blood input function may be associated with a second time period between the injection time and a start time of the first time period. The one or more processors may determine kinetic parameters of the kinetic model based on the PET data, the first portion of the blood input function, and the integral of the second portion of the blood input function. The kinetic parameters may indicate a metabolism of the tracer in the subject.

According to yet another aspect of the present disclosure, a non-transitory computer readable medium may comprise at least one set of instructions. The at least one set of instructions may be executed by one or more processors of a computer server. The one or more processors may direct a positron emission tomography (PET) scanner to perform scans of a subject injected with a tracer during a first time period. The tracer may be injected into the subject at an injection time prior to the first time period. The one or more processors may generate PET images by reconstructing the PET data that are generated by the PET scanner based on the scans of the subject. The one or more processors may determine a first portion of a blood input function of the tracer in the subject based on the PET images. The first portion of the blood input function may be associated with the first time period. The one or more processors may determine an integral of a second portion of the blood input function based on a kinetic model, the PET data, and the first portion of the blood input function. The second portion of the blood input function may be associated with a second time period between the injection time and a start time of the first time period. The one or more processors may determine kinetic parameters of the kinetic model based on the PET data, the first portion of the blood input function, and the integral of the second portion of the blood input function. The kinetic parameters may indicate a metabolism of the tracer in the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
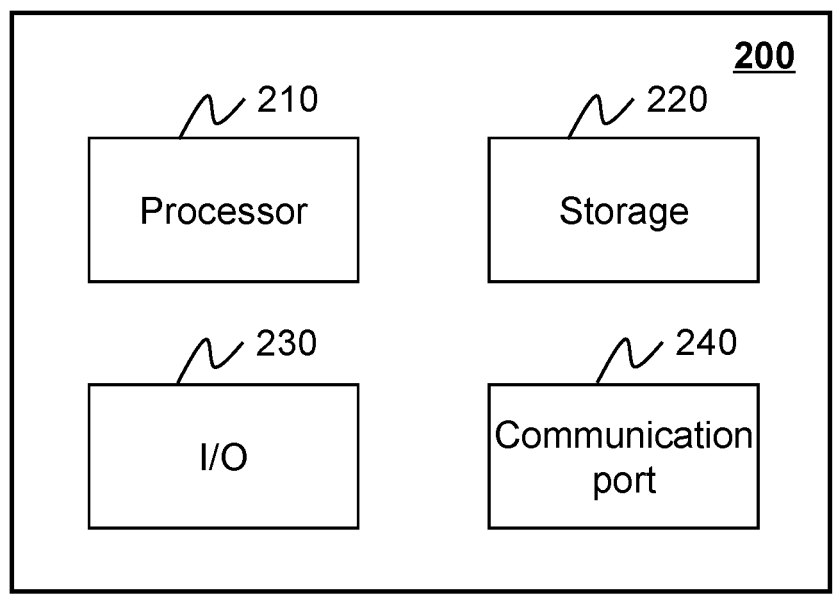
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for determining kinetic parameters in dynamic PET imaging based on the Patlak estimation. To estimate the kinetic parameters, a blood input function may be obtained to be the input to the Patlak estimation. To this end, a tracer may be injected into a subject. The PET scanner may perform scans of the subject after a distribution of the tracer in the subject reaches a steady state instead of from the injection time of the tracer. A plurality of PET images may be generated based on PET data generated during the scans. A first portion of the blood input function may be determined by processing the PET images. The first portion of the blood input function may correspond to the scan time. An integral of the second portion of the blood input function may be determined based on the PET data, the Patlak estimation, and the first portion of the blood input function. The kinetic parameters may be determined based on the Patlak estimation, the PET data, the first portion of the blood input function, and the integral of the second portion of the blood input function. The kinetic parameters may provide information regarding the tracer metabolism in the subject. For instance, the kinetic parameter may be used to determine whether there is a lesion in the subject.

The following description is provided to help better understanding systems and/or methods for determining kinetic parameters in Dynamic PET imaging. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
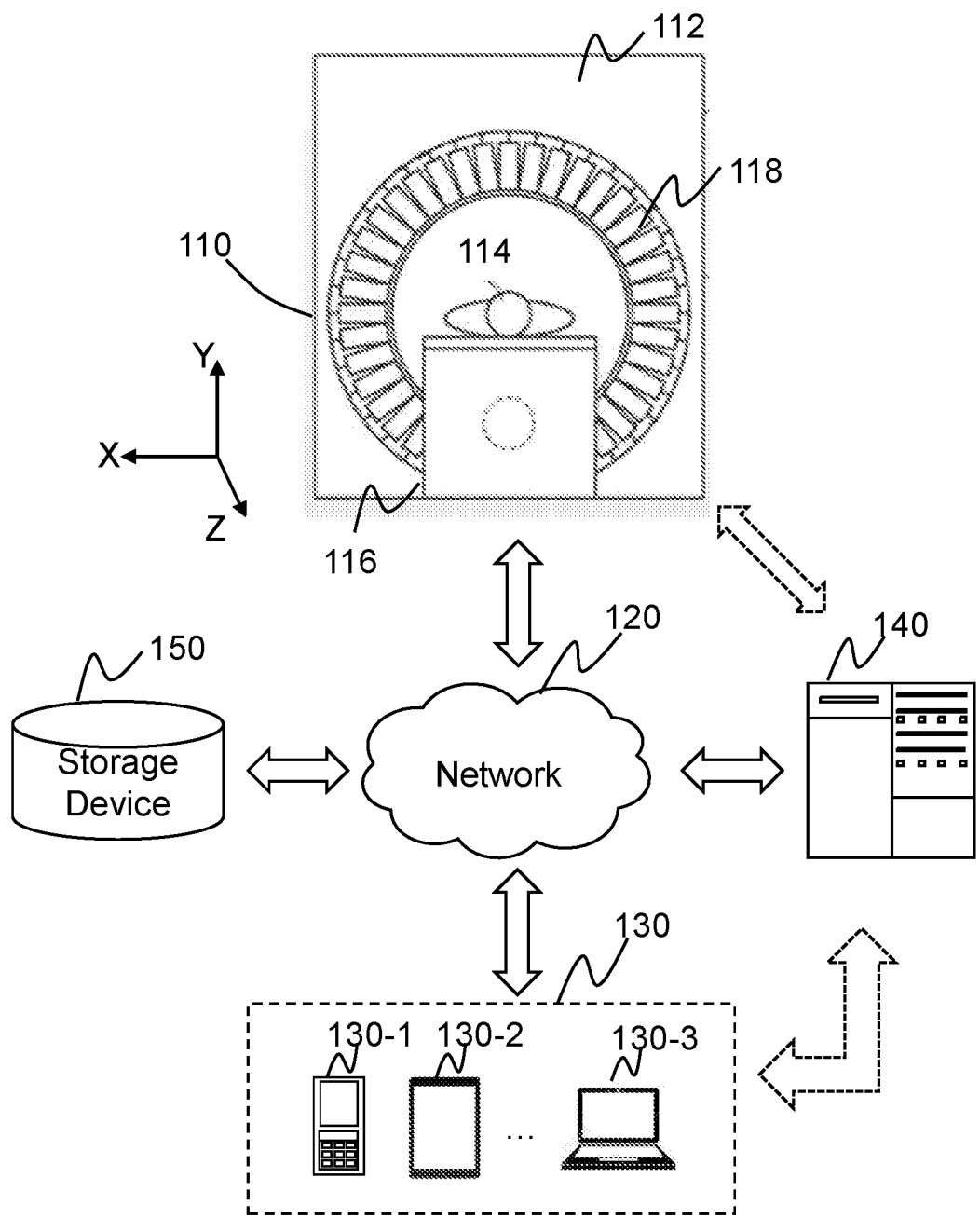
FIG. 1 is a schematic diagram illustrating an exemplary positron emission tomography (PET) system according to some embodiments of the present disclosure.

FIG. 1 is a schematic diagram illustrating an exemplary positron emission tomography (PET) system according to some embodiments of the present disclosure.

The PET system 100 may include a PET scanner 110, a network 120, a terminal 130, a processing device 140, and a storage device 150. The components in the PET system 100 may be connected in one or more of various manners. Merely by way of example, the PET scanner 110 may be connected to the processing device 140 through the network 120. As another example, the PET scanner 110 may be connected to the processing device 140 directly (shown as the bi-directional arrow in dotted line linking the PET scanner 110 and the processing device 140). As another example, the processing device 140 may be connected to the storage device 150 through the network 120 or directly. As a further example, the processing device 140 may be connected to a terminal device (e.g., 130-1, 130-2, 130-3, etc.) through the network 120. As still a further example, the processing device 140 may be connected to a terminal device (e.g., 130-1, 130-2, 130-3, etc.) directly (shown as the bi-directional arrow in dotted line linking the terminal 130 and the processing device 140).

The PET scanner 110 may include a gantry 112, a table 116, and a detector 118. A subject 114 injected with a tracer (e.g., radiopharmaceutical) may be placed on the table 116. The gantry 112 may support the detector 118. The gantry 112 may form a detection tunnel (not shown in FIG. 1).

The tracer refers to a radioactive substance that may decay and emit positrons. The radiopharmaceutical refers to a drug having radioactivity, which is introduced into the subject 114 for the purposes of diagnosis and/or treatment. The subject 114 may be biological or non-biological. Merely by way of example, the subject 114 may include a patient, a man-made object (e.g., a phantom), or the like. As another example, the subject 114 may include a specific portion, organ, and/or tissue of the patient. For example, the subject 114 may include the head, the brain, the neck, the body, a shoulder, an arm, the thorax, the heart, the stomach, a blood vessel, a soft tissue, a knee, a foot, or the like, of a patient, or any combination thereof.

In some embodiments, the detector 118 may include a plurality of detector rings arranged along the axial direction (e.g., Z-axis direction in FIG. 1). The plurality of detector rings may be located around the detection tunnel. A detector ring may include a plurality of detector units arranged along the circumference of the detector ring. The plurality of detector units may detect photons (e.g., gamma photons) produced by annihilation events.

In some embodiments, positrons generated by the nucleus of a radiotracer may travel through the subject 114 until they encounter electrons. When a positron and an electron collide, annihilation may occur. The electron-positron annihilation may simultaneously generate two 511-kiloelectron volt (511 keV) gamma photons (i.e., a photon pair) traveling in substantially opposite directions along a line. The photon pair may be detected by a pair of oppositely disposed detector units (herein referred to as a detector pair). A photon pair arriving at the detector pair within a short time window may be called a coincidence or an event. The coincidence may be assumed to occur along a line connecting the detector pair, and the line may be called as a "line of response" (LOR). The detector 118 may obtain counts of coincidences based on the LORs for detected coincidences and time points at which the coincidences occurred.

In some embodiments, the PET scanner 110 may also be a multi-modality scanner, for example, a tomography-positron emission tomography (CT-PET) scanner.

The network 120 may facilitate exchange of information and/or data. In some embodiments, one or more components in the PET system 100 (e.g., the PET scanner 110, the terminal 130, the processing device 140, or the storage device 150) may send information and/or data to another component(s) in the PET system 100 via the network 120. For example, the processing device 140 may obtain PET data from the PET scanner 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. The terminal 130 may remotely operate the PET scanner 110. In some embodiments, the terminal 130 may operate the PET scanner 110 via a wireless connection. In some embodiments, the terminal 130 may receive information and/or instructions inputted by a user, and transmit the received information and/or instructions to the PET scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the PET scanner 110, the terminal 130, or the storage device 150. For example, the processing device 140 may process the PET data obtained from the PET scanner 110 and reconstruct an image based on the obtained PET data. In some embodiments, the processing device 140 may be a single server or a server group. The server group may be centralized or distributed. In some embodiments, the processing device 140 may be local or remote. For example, the processing device 140 may access information and/or data stored in the PET scanner 110, the terminal 130, and/or the storage device 150 via the network 120. As another example, the processing device 140 may be directly connected to the PET scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the PET scanner 110, the terminal 130 and/or the processing device 140. For example, the storage device 150 may store images generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to determine kinetic parameters. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the PET system 100 (e.g., the processing device 140, the terminal 130). One or more components of the PET system 100 may access the data or instructions stored in the storage device 150 via the network 120. In some embodiments, the storage device 150 may be directly connected to or communicate with one or more components in the PET system 100 (e.g., the processing device 140, the terminal 130). In some embodiments, the storage device 150 may be part of the processing device 140.

The PET system 100 may generate static PET images and/or dynamic PET images. The PET images may be two-dimensional (2D) or three-dimensional (3D). In contrast with static PET images, dynamic PET images may provide rich information associated with the dynamic changes in tracer uptake, for example, the tracer metabolism over time in tissue. Changes in uptake may be estimated by comparing a plurality of dynamic PET images of the subject acquired over different time intervals/frames. The plurality of dynamic PET images may be used for quantitative kinetic analysis. The quantitative kinetic analysis may include determining kinetic parameters based on dynamic PET data by using kinetic models. The kinetic parameters may describe the tracer behavior in a homogeneous region of tissue, such as the myocardium or the entire striatum in a brain image. A user (e.g., a doctor or a clinician) may further make a clinical diagnose by analyzing the kinetic parameters, for example, determining a tumor lesion, etc.

FIG. 2 is a schematic diagram illustrating exemplary hardware and/or software components of a computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may process data obtained from the PET scanner 110, the terminal 130, the storage device 150, or any other component of the PET system 100. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two different processors jointly or separately in the computing device 200 (e.g., a first processor executes operation A and a second processor executes operation B, or the first and second processors jointly execute operations A and B).

The storage 220 may store data/information obtained from the PET scanner 110, the terminal 130, the storage device 150, or any other component of the PET system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining kinetic parameters.

The I/O 230 may input or output signals, data, or information. In some embodiments, the I/O 230 may enable user interaction with the processing device 140. For example, the processing device may display an image through the I/O 230. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the PET scanner 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
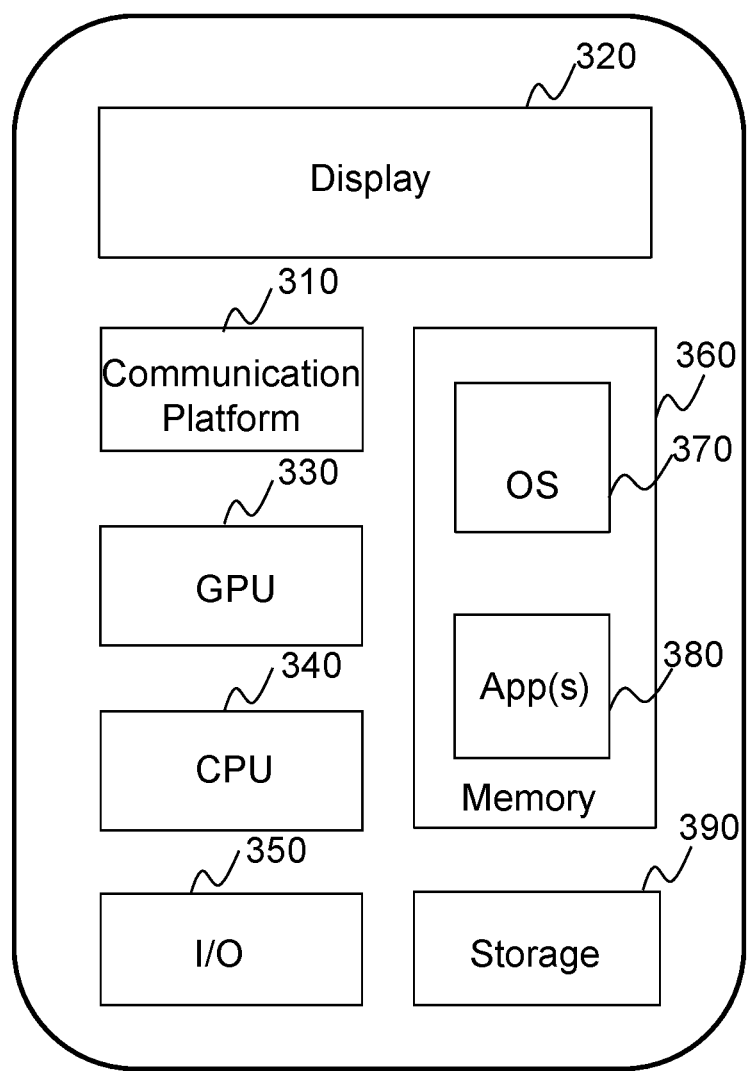
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
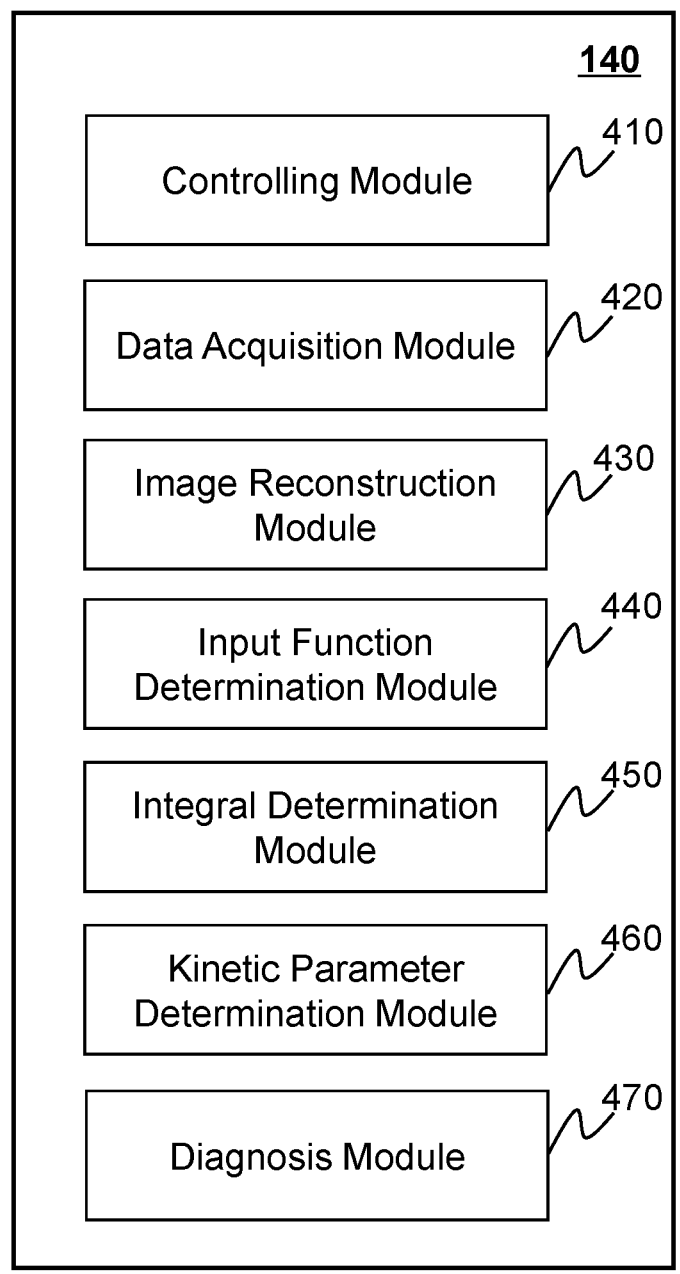
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include a controlling module 410, a data acquisition module 420, an image reconstruction module 430, an input function determination module 440, an integral determination module 450, a kinetic parameter determination module 460, and a diagnosis module 470.

The controlling module 410 may be configured to direct the PET scanner 110 to perform scans of a subject (e.g., a region of interest (ROI) of the subject) injected with a tracer during a first time period in which the distribution of the tracer is deemed in a steady state in the subject. The first time period (also referred to as a scan time) may be after an injection time at which the tracer is injected into the subject.

The subject may be biological or non-biological. Merely by way of example, the subject may include a patient, a man-made object (e.g., a phantom), or the like. As another example, the subject may include a specific portion, organ, and/or tissue of the patient. For example, the subject may include the head, the brain, the neck, the body, a shoulder, an arm, the thorax, the heart, the stomach, a blood vessel, a soft tissue, a knee, a foot, or the like, of a patient, or any combination thereof.

The tracer refers to a radioactive substance that may decay and emit positrons. As used in the present disclosure, an exemplary tracer for PET imaging may be an irreversible tracer such as $^{18}$F-fluorodeoxyglucose ($^{18}$F-FDG).

Taking the $^{18}$F-FDG as an example, after the $^{18}$F-FDG is injected (e.g., a bolus intravenous injection) into the subject, at least a portion of the injected $^{18}$F-FDG may move to the interstitial fluid. The $^{18}$F-FDG in the interstitial fluid may move into cells under the action of glucose transporter 1 (GLUT1) on the cell membrane or return back to the blood. The $^{18}$F-FDG in the cells may be phosphorylated into $^{18}$F-FDG-6P by hexokinase. The $^{18}$F-FDG-6P is an irreversible tracer that is neither metabolized nor dephosphorylated to travel back to the blood within a short time (e.g., a time period from the injection time to the end of the scans of the subject). During the scans of the subject, once the $^{18}$F-FDG moves into the cells, the $^{18}$F-FDG is assumed to be irreversibly trapped in the cells. As a result, more $^{18}$F-FDG may accumulate in tissue having a lesion (e.g., a tumor), which is with relatively stronger metabolism than normal tissue.

In the present disclosure, after the tracer is injected into the subject, the controlling module 410 may direct the PET scanner 110 to perform scans of the subject only after the distribution of the tracer is deemed in the steady state in the subject. In some embodiments, the start time of the first time period may be equal to or after a balance time point at which the distribution of the tracer in the subject is deemed to have reached the steady state. In the steady state, there may be a dynamic balance between the concentration of the tracer in the blood and the concentration of the tracer in tissue. For example, in the steady state, a ratio of the concentration of the tracer in the blood and the concentration of the tracer in tissue may be constant or substantially constant. As used herein, the concentration of the tracer in the blood and/or in tissue being "substantially constant" may indicate that the change of the concentration of the tracer in the blood and/or in tissue is lower than a threshold over a time period. The threshold may be 20%, 15%, 10%, 5%, etc., of the tracer concentration in the blood/tissue. The time period may be 10 minutes, 8 minutes, 5 minutes, 3 minutes, 2 minutes, 1 minute, 30 seconds, etc.

In some embodiments, the balance time point of a tracer may be obtained according to clinical experiments. During the process for determining the balance time point of a tracer, the tracer concentration in the blood or in tissue may be estimated based on blood sampling or image analysis. Different types of tracers may have different balance time points. For example, the balance time point of the $^{18}$F-FDG may be approximately 40 minutes after the $^{18}$F-FDG is injected into the subject. The PET scanner 110 may perform scans of the subject from 40 minutes to 80 minutes after the $^{18}$F-FDG is injected into the subject.

In some embodiments, a duration (also referred to as a time frame) of each scan of the scans of the subject may be the same or different. For example, the PET scanner 110 may perform 30 scans of the subject, such as 4 scans whose duration is 20 seconds per scan, 4 scans whose duration is 40 seconds per scan, 4 scans whose duration is 60 seconds per scan, 4 scans whose duration is 180 seconds per scan, and 14 scans whose duration is 300 seconds per scan. In some embodiments, there may be a time interval or no time interval between two adjacent scans. Merely by way of example, a second scan immediately following a first scan may start when the first scan is finished.

In some embodiments, the PET scanner 110 may perform the scans of the subject at a single bed position (or fixed field of view, FOV) during the first time period. In some embodiments, during the first time period, the PET scanner 110 may perform the scans of the subject through repeated passes each of which includes multiple bed positions. During a pass, the multiple bed position scans may be taken in sequence (one bed position after another bed position in real time). At each bed position the subject is therefore scanned, non-continuously, for multiple times (e.g., equal to the number/count of the passes).

In some embodiments, before the scans of the subject (e.g., before the start time of the first time period), a user (e.g., a doctor or an imaging technician) of the PET system 100 may set a scan protocol through, for example, the I/O 230 of the processing device 140 and/or the I/O 350 of the terminal 130. The PET scanner 110 may perform the scans of the subjects based on the scan protocol. The scan protocol may include the type of the tracer, the balance time point of the tracer, the injection time, the half-life of the tracer, the first time period, the start time of the first time period, the end time of the first time period, the time frames of the scans of the subjects, the number of the scans of the subject, or the like, or any combination thereof.

Figure 7:
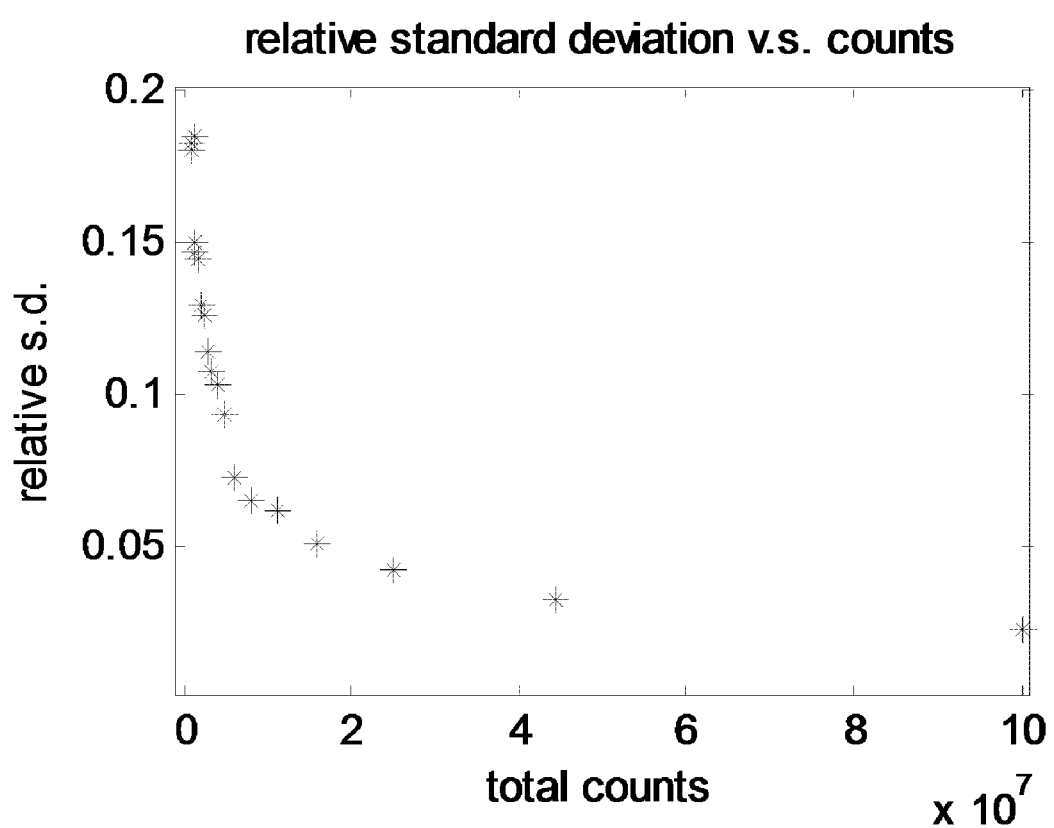
FIG. 7 is a schematic diagram illustrating an example that represents the relative standard deviation of an estimated integral of a blood input function versus different count levels for time frames of PET scans according to some embodiments of the present disclosure.

In some embodiments, the more the PET data is, the more accurate the blood input function (e.g., the first portion of the blood input function and the integral of the second portion of the blood input function) may be (as shown in FIG. 7). Because the tracer decays over time, a start time of the first time period closer to the balance time point of the tracer may lead to more and richer PET data within the same scan time (e.g., the same first time period).

The data acquisition module 420 may be configured to obtain PET data generated by the PET scanner 110 based on the scans of the subject.

The generated PET data may relate to a plurality of coincidences detected by the detector 118 in FIG. 1 during the scans of the subject. For example, the PET data may include a total number or count of photon pairs detected by each detector pair in the detector 118 of the PET scanner 110, position information related to occurrence of the plurality of coincidences along the LORs, time information (e.g., an arrival time at the detector 118 for each photon pair, and/or an occurrence time for each photon pair) of the plurality of coincidences, or the like, or any combination thereof. In some embodiments, the PET data may be in the form of list-mode data. In some embodiments, the PET data may be in the form of sinogram data. For example, the list-mode data may be projected to the sinogram data. In some embodiments, the PET data may be stored in a storage medium (e.g., the storage device 150 and/or the storage 220 of the processing device 140) of the PET system 100. The data acquisition module 420 may retrieve the PET data from the storage medium of the PET system 100 for further processing. In some embodiments, the data acquisition module 420 may obtain the PET data from the PET scanner 110 directly for further processing.

The image reconstruction module 430 may be configured to generate PET images based on the scans of the subject by reconstructing the PET data (e.g., the list-mode data or the sinogram data). In some embodiments, the image reconstruction module 430 may reconstruct a PET image based on the PET data generated during one of the scans of the subject. For example, if the PET scanner 110 performs 30 scans of the subject, the image reconstruction module 430 may reconstruct 30 PET images each of which corresponds to one of the 30 scans of the subject.

Exemplary image reconstruction techniques may include filtered back projection (FBP), an algebraic reconstruction technology (ART), a statistical reconstruction (SR) algorithm, or the like, or any combination thereof. It should be understood by those skilled in the art that the image reconstruction technique may be varied. All such variations are within the protection scope of the present disclosure.

The input function determination module 440 may be configured to determine a first portion of a blood input function (also referred to as an arterial time-activity curve (TAC)) of the tracer in the subject based on the PET images (e.g., the dynamic PET images). The first portion of the blood input function may indicate activities (or concentrations) of the tracer during the first time period.

Merely by way of example, the input function determination module 440 may determine a same ROI or volume of interest (VOI) for each of the PET images. The ROI or VOI may include at least one artery. For each PET image, the input function determination module 440 may determine an average of pixel or voxel values related to the artery in the ROI or VOI. The input function determination module 440 may assess, based on the average, the activity (or concentration) of the tracer in the blood during the time frame of a scan corresponding to the PET image. In some embodiments, the activity (or concentration) of the tracer in the blood during a time frame of a scan may be considered constant during the time frame; the average of pixel or voxel values related to the artery in the ROI or VOI during the time frame may be considered representative of the activity (or concentration) during the time frame. In some embodiments, the activity (or concentration) of the tracer in the blood during a time frame of a scan may vary during the time frame; the average of pixel or voxel values related to the artery in the ROI or VOI during the time frame may be considered corresponding to the activity (or concentration) at a time point during the time frame, e.g., the midpoint of the time frame, and representative of the activity (or concentration) during the time frame. For example, if the PET scanner 110 performs 30 scans of the subject and the image reconstruction module 430 generates 30 PET images based on the 30 scans of the subject, the input function determination module 440 may obtain 30 activity (or concentration) values of the tracer in the blood at 30 time points within the first time period by processing the 30 PET images. It should be noted that the process for determining the activity of the tracer in the blood based on a PET image is merely provided for the purposes of illustration, and not intended to limit the scope of the present disclosure. For persons having ordinary skills in the art, another relevant process may also be used to determine the activity of the tracer in the blood based on a PET image.

The input function determination module 440 may determine the first portion of the blood input function by curve fitting of the activity values of the tracer in the blood at a plurality of time points. In some embodiments, the fitting may include interpolation, extrapolation, smoothing, regression analysis, the least squares algorithm, or the like, or any combination thereof. Exemplary interpolation algorithms may include Lagrange interpolation, Newton interpolation, Hermite interpolation, piecewise interpolation, spline interpolation, linear interpolation, or the like, or a combination thereof. Exemplary extrapolation algorithms may include linear extrapolation, polynomial extrapolation, conic extrapolation, French curve extrapolation, or the like, or a combination thereof. Exemplary regression analysis may include linear regression, nonlinear regression, multiple regression, logistic regression, partial regression, or the like, or a combination thereof.

In some embodiments, the process described above for determining the first portion of the blood input function may be applicable when the PET scanner 110 performs the scans of the subject at a single bed position (or fixed field of view, FOV) during the first time period.

In some embodiments, when the PET scanner 110 performs the scans of the subject at multiple bed positions during the first time period, the input function determination module 440 may determine the first portion of the blood input function based on the PET data of the scans performed at the multiple bed positions. For example, the input function determination module 440 may determine an ROI or VOI for each of the PET images for the multiple bed positions. The ROI or VOI may include at least one artery. The ROIs or VOIs related to a same bed position may be same or at least partially overlap. The input function determination module 440 may determine an activity of the tracer for each of the PET images based on a process similar to that described above. The input function determination module 440 may modify the activity of each of the PET images based on the size of the artery in the respective ROI or VOI. Alternatively, the artery in the ROI or VOI in one of the PET images may be chosen as the standard and the input function determination module 440 may perform the modification of the rest of activities based on the standard artery size. The modification of the activities may be done by correction technologies including, e.g., partial volume effect (PVE) correction. The input function determination module 440 may combine the modified activities (and the unmodified, standard activity) to generate the first portion of the blood input function. For example, the input function determination module 440 may stitch together the modified activities (and the unmodified, standard activity) in a chronological order to generate the first portion of the blood input function. More descriptions regarding the embodiments with respect to multiple bed positions may be found in, e.g., U.S. Pat. No. 8,831,323 B2, the contents of which are hereby incorporated by reference.

The integral determination module 450 may be configured to determine an integral of a second portion of the blood input function based on a kinetic model, the PET data, and the first portion of the blood input function. The second portion of the blood input function may correspond to a second time period between the injection time and the start time of the first time period. For example, the second time period may be from the injection time to the start time of the first time period, or a portion thereof.

As used in the present disclosure, the kinetic model may be a two-compartment model. In the two-compartment model, one of the two compartments may represent blood, and the other one of the two compartments may represent tissue.

In some embodiments, the integral determination module 450 may determine a Patlak estimation based on the two-compartment model for irreversible tracers. The Patlak estimation may represent a dynamic behavior of the irreversible tracers through transfer between the two compartments. The Patlak estimation may represent a relationship between the activity (or concentration) of the tracer in tissue and the activity (or concentration) of the tracer (e.g., the irreversible tracer) in blood. When the distribution of the tracer in the subject reaches the steady state, the Patlak plot may become linear. The slope of the linear phase of the Patlak plot may indicates the net transfer rate between the two compartments (e.g., tissue and blood). The intercept of the linear phase of the Patlak plot may represent the distribution volume of the tracer in the compartment of blood.

In some embodiments, the Patlak plot may be applicable to pixels or voxels of the PET images. In this case, a slope parameter (also referred to as slope value) and an intercept parameter (also referred to as intercept value) related to at least one pixel or voxel of the PET images (e.g., the pixels or voxels in the ROI or VOI of the PET images) may be determined. The kinetic parameters may include the slope parameters and the intercept parameters of the at least one voxel or pixel of the PET images.

In some embodiments, the Patlak estimation may represent a relationship of the blood input function, the PET data, and the kinetic parameters. For example, the Patlak estimation may be represented by Equation (1) as below:

$$\int_{t(l)}^{t(l)+\Delta t} y_i(t)dt = \Sigma_j P_{ij}(K_j \int_{t(l)}^{t(l)+\Delta t}(\int_0^t \text{bld}(\tau)d\tau)dt + q_j \int_{t(l)}^{t(l)+\Delta t}\text{bld}(t)dt) + \int_{t(l)}^{t(l)+\Delta t}[r_i(t)+s_i(t)]dt,\ t>T_0 \quad (1),$$

where $y_i(t)$ denotes a count of photon pairs generated at LOR i at time t; t(l) denotes a start time of time frame l; $\Delta t$ denotes a duration of time frame l; $P_{ij}$ denotes a response matrix including a plurality of elements, and each element represents a probability of a photon pair being detected by a detector pair that is connected by LOR i when the photon pair is generated at a location corresponding to voxel (or pixel) j of an PET image associated with time frame l; $K_j$ and $q_j$ are the Patlak parameters, in which $K_j$ denotes a slope value of the linear phase of the Patlak plot for voxel (or pixel) j, and $q_j$ denotes an intercept value of the linear phase of the Patlak plot for voxel (or pixel) j; bld($\tau$) and/or bld(t) denote an activity (or concentration) of the tracer at a certain time point (e.g., t or $\tau$) in the blood input function; $r_i(t)$ and $s_i(t)$ denote the random coincidence rate and the scattered coincidence rate along LOR i at time t, respectively; and $T_0$ denotes the start time of the first time period. In some embodiments, the $y_i(t)$, $P_{ij}$, $r_i(t)$, and $s_i(t)$ may be determined based on the PET data.

As illustrated in Equation (1), Equation (1) may be associated with one LOR. In order to make the Patlak estimation associated with all LORs related to the detector 118, Equation (1) may be transformed to Equation (2) as below:

$$\Sigma_i \int_{t(l)}^{t(l)+\Delta t}\{y_i(t)-[r_i(t)+s_i(t)]\}dt = \Sigma_i \Sigma_j P_{ij}(K_j \int_{t(l)}^{t(l)+\Delta t}(\int_0^t \text{bld}(\tau)d\tau)dt + q_j \int_{t(l)}^{t(l)+\Delta t}\text{bld}(t)dt),\ t>T_0 \quad (2),$$

Equation (2) may be further transformed to Equation (3) as below:

$$\Sigma_i \int_{t(l)}^{t(l)+\Delta t}\{y_i(t)-[r_i(t)+s_i(t)]\}dt = \Sigma_i \Sigma_j P_{ij}(K_j \int_{t(l)}^{t(l)+\Delta t}(\int_0^{T_0}\text{bld}(\tau)d\tau + \int_{T_0}^t \text{bld}(\tau)d\tau)dt + q_j \int_{t(l)}^{t(l)+\Delta t}\text{bld}(t)dt),\ t>T_0 \quad (3),$$

where $\int_0^{T_0} \text{bld}(\tau)d\tau$ denotes an integral of the second portion of the blood input function.

From Equation (3), if the PET scanner 110 starts to perform scans of the subject after the distribution of the tracer is deemed to have reached the steady state, information that need to be input to the Patlak estimation to estimate the kinetic parameters may include at least one of the integral of the blood input function corresponding to the second time period between the injection time and the start time of the first time period (e.g., the integral of the second portion of the blood input function), instead of the curve of the blood input function corresponding to the second time period, or the curve of the blood input function corresponding to the first time period. Equation (3) may provide the theoretical basis for scanning the subject after the distribution of the tracer reaches the steady state instead of from the injection time.

In some embodiments, let $$Y(l) = \Sigma_i \int_{t(l)}^{t(l)+\Delta t}\{y_i(t)-[r_i(t)+s_i(t)]\}dt \quad (4),$$

$$C = \int_0^{T_0} \text{bld}(\tau)d\tau \quad (5),$$

$$B1(l) = \int_{t(l)}^{t(l)+\Delta t}(\int_{T_0}^t \text{bld}(\tau)d\tau)dt \quad (6),$$

$$B2(l) = \int_{t(l)}^{t(l)+\Delta t}\text{bld}(t)dt \quad (7),$$

$$PK = \Sigma_j \Sigma_i P_{ij} K_j \quad (8), \text{ and}$$

$$Pq = \Sigma_j \Sigma_i P_{ij} q_j \quad (9).$$

Equation (3) may be transformed to Equation (10) as below based on Equations (4)-(9):

where Y(l) may represent the PET data that is generated during time frame l excluding the data related to the random coincidences and the scattered coincidences.

If the PET scanner 110 performs n scans of the subject, Equation (10) may be further transformed to a matrix equation (e.g., Equation (11)) as below:

$$\begin{pmatrix} Y(1) \\ . \\ . \\ . \\ Y(n) \end{pmatrix} = \begin{pmatrix} B1(1) + C\Delta t & B2(1) \\ . & . \\ . & . \\ . & . \\ B1(n) + C\Delta t & B2(n) \end{pmatrix} \begin{pmatrix} PK \\ Pq \end{pmatrix}, t > T_0. \quad (11)$$

In some embodiments, the integral determination module 450 may determine a target function based on the Patlak estimation (e.g., Equation (11)), and determine the integral of the second portion of the blood input function by solving the target function. In some embodiments, the target function may represent a relationship of the PET data generated during the first time period, the first portion of the blood input function, and the integral of the second portion of the blood input function.

In some embodiments, different algorithms for determining the integral of the second portion of the blood input function may correspond to different target functions. For example, the integral determination module 450 may determine the integral of the second portion of the blood input function using a least squares (LS) algorithm. Assuming that the noise distribution of the PET data conforms with the Gaussian noise model, the integral determination module 450 may determine a target function expressed by Equation (12) as below:

$$\tilde{C} = \min_C |Y - (B + K)((B + K)^T (B + K))^{-1} (B + K)^T Y|^2, \quad (12)$$

$$t > T_0,$$

where $\tilde{C}$ represents a target function value, $$Y = \begin{pmatrix} Y(1) \\ . \\ . \\ . \\ Y(n) \end{pmatrix}, B = \begin{pmatrix} B1(1) & B2(1) \\ . & . \\ . & . \\ . & . \\ B1(n) & B2(n) \end{pmatrix}, \text{ and } K = \begin{pmatrix} C\Delta t & 0 \\ . & . \\ . & . \\ . & . \\ C\Delta t & 0 \end{pmatrix}.$$

It should be noted that the LS algorithm is merely provided for the purposes of illustration, and not intended to limit the scope of the present disclosure. For persons having ordinary skills in the art, other relevant algorithms may also be used to determine the integral of the second portion of the blood input function, for example, an expectation maximization (EM) algorithm.

The kinetic parameters determination module 460 may be configured to determine kinetic parameters of the kinetic model based on the PET data, the first portion of blood input function, and the integral of the second portion of the blood input function. For example, the kinetic parameters determination module 460 may apply the PET data, the first portion of the blood input function, and the second portion of the blood input function into the kinetic model (e.g., the Patlak estimation represented by Equation (1), Equation (2), Equation (3), Equation (10), or Equation (11)) and determine the kinetic parameters $K_j$ and $q_j$. It should be noted that there is no limitation on approaches for determining the kinetic parameter of the Patlak estimation, and any relevant approach may be used in the present disclosure.

In some embodiments, the kinetic parameter determination module 460 may reconstruct a Patlak slope image based on $K_j$ and reconstruct a Patlak intercept image based on $q_j$.

The diagnosis module 470 may be configured to determine whether there is a lesion in the subject (e.g., the ROI of the subject) based on the kinetic parameters. Merely by way of example, the diagnosis module 470 may determine whether there is a lesion in the subject and the lesion location by comparing the Patlak slope $K_j$ and the Patlak intercept $q_j$ to normal Patlak slope values and normal Patlak intercept values. In some embodiments, the normal Patlak slope values and the normal Patlak intercept values may be determined based on clinical experiments and/or empirical data. The normal Patlak slope values and the normal Patlak intercept values may be stored in a storage medium (e.g., the storage device 150 and/or the storage 220) of the PET system 100. In some embodiments, the diagnosis module 470 may output a diagnosis report indicating whether there is a lesion in the subject and the lesion location through, for example, the I/O 230 of the processing device 140 and/or the I/O 350 of the terminal 130.

Alternatively, the kinetic parameter determination module 460 may output the kinetic parameters (or the Patlak slope image and the Patlak intercept image) through, for example, the I/O 230 of the processing device 140 and/or the I/O 350 of the terminal 130. A user of the PET system 100 may make a diagnosis based on the kinetic parameters. In this case, the diagnosis module 470 may be omitted.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the input function determination module 440 may be integrated into the integral determination module 450 as a single module which may both determine the first portion of the blood input function and the integral of the second portion of the blood input function.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of components of the processing device 140 may include a storage apparatus. Additionally or alternatively, the components of the processing device 140 may share a common storage apparatus.

Figure 5:
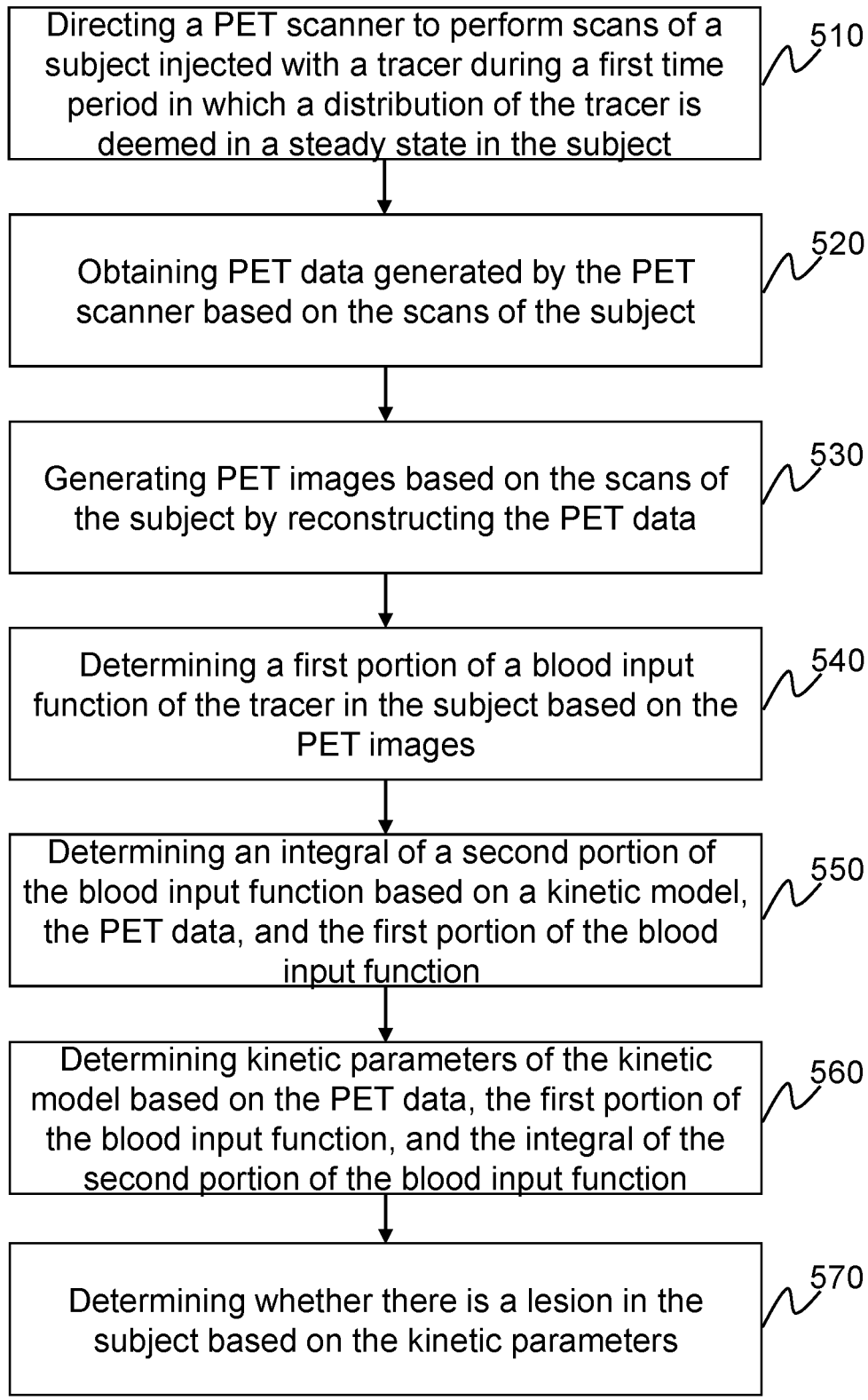
FIG. 5 is a flowchart illustrating an exemplary process for determining kinetic parameters according to some embodiments of the present disclosure.

FIG. 5 is a flowchart illustrating an exemplary process for determining kinetic parameters according to some embodiments of the present disclosure. The process 500 may be implemented in the PET system 100 illustrated in FIG. 1. For example, the process 500 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the controlling module 410 may direct the PET scanner 110 to perform scans of a subject (e.g., a region of interest (ROI) of the subject) injected with a tracer during a first time period in which the distribution of the tracer is deemed in a steady state in the subject. The first time period (also referred to as a scan time) may be after an injection time at which the tracer is injected into the subject.

The subject may be biological or non-biological. Merely by way of example, the subject may include a patient, a man-made object (e.g., a phantom), or the like. As another example, the subject may include a specific portion, organ, and/or tissue of the patient. For example, the subject may include the head, the brain, the neck, the body, a shoulder, an arm, the thorax, the heart, the stomach, a blood vessel, a soft tissue, a knee, a foot, or the like, of a patient, or any combination thereof.

The tracer refers to a radioactive substance that may decay and emit positrons. As used in the present disclosure, an exemplary tracer for PET imaging may be an irreversible tracer such as $^{18}$F-fluorodeoxyglucose ($^{18}$F-FDG).

Taking the $^{18}$F-FDG as an example, after the $^{18}$F-FDG is injected (e.g., a bolus intravenous injection) into the subject, at least a portion of the injected $^{18}$F-FDG may move to the interstitial fluid. The $^{18}$F-FDG in the interstitial fluid may move into cells under the action of glucose transporter 1 (GLUT1) on the cell membrane or return back to the blood. The $^{18}$F-FDG in the cells may be phosphorylated into $^{18}$F-FDG-6P by hexokinase. The $^{18}$F-FDG-6P is an irreversible tracer that is neither metabolized nor dephosphorylated to travel back to the blood within a short time (e.g., a time period from the injection time to the end of the scans of the subject). During the scans of the subject, once the $^{18}$F-FDG moves into the cells, the $^{18}$F-FDG is assumed to be irreversibly trapped in the cells. As a result, more $^{18}$F-FDG may accumulate in tissue having a lesion (e.g., a tumor), which is with relatively stronger metabolism than normal tissue.

In the present disclosure, after the tracer is injected into the subject, the controlling module 410 may direct the PET scanner 110 to perform scans of the subject only after the distribution of the tracer is deemed in the steady state in the subject. In some embodiments, the start time of the first time period may be equal to or after a balance time point at which the distribution of the tracer in the subject is deemed to have reached the steady state. In the steady state, there may be a dynamic balance between the concentration of the tracer in the blood and the concentration of the tracer in tissue. For example, in the steady state, a ratio of the concentration of the tracer in the blood and the concentration of the tracer in tissue may be constant or substantially constant. As used herein, the concentration of the tracer in the blood and/or in tissue being "substantially constant" may indicate that the change of the concentration of the tracer in the blood and/or in tissue is lower than a threshold over a time period. The threshold may be 20%, 15%, 10%, 5%, etc., of the tracer concentration in the blood/tissue. The time period may be 10 minutes, 8 minutes, 5 minutes, 3 minutes, 2 minutes, 1 minute, 30 seconds, etc.

In some embodiments, the balance time point of a tracer may be obtained according to clinical experiments. During the process for determining the balance time point of a tracer, the tracer concentration in the blood or in tissue may be estimated based on blood sampling or image analysis. Different types of tracers may have different balance time points. For example, the balance time point of the $^{18}$F-FDG may be approximately 40 minutes after the $^{18}$F-FDG is injected into the subject. The PET scanner 110 may perform scans of the subject from 40 minutes to 80 minutes after the $^{18}$F-FDG is injected into the subject.

In some embodiments, a duration (also referred to as a time frame) of each scan of the scans of the subject may be the same or different. For example, the PET scanner 110 may perform 30 scans of the subject, such as 4 scans whose duration is 20 seconds per scan, 4 scans whose duration is 40 seconds per scan, 4 scans whose duration is 60 seconds per scan, 4 scans whose duration is 180 seconds per scan, and 14 scans whose duration is 300 seconds per scan. In some embodiments, there may be a time interval or no time interval between two adjacent scans. Merely by way of example, a second scan immediately following a first scan may start when the first scan is finished.

In some embodiments, the PET scanner 110 may perform the scans of the subject at a single bed position (or fixed field of view, FOV) during the first time period. In some embodiments, during the first time period, the PET scanner 110 may perform the scans of the subject through repeated passes each of which includes multiple bed positions. During a pass, the multiple bed position scans may be taken in sequence (one bed position after another bed position in real time). At each bed position the subject is therefore scanned, non-continuously, for multiple times (e.g., equal to the number/count of the passes).

In some embodiments, before the scans of the subject (e.g., before the start time of the first time period), a user (e.g., a doctor or an imaging technician) of the PET system 100 may set a scan protocol through, for example, the I/O 230 of the processing device 140 and/or the I/O 350 of the terminal 130. The PET scanner 110 may perform the scans of the subjects based on the scan protocol. The scan protocol may include the type of the tracer, the balance time point of the tracer, the injection time, the half-life of the tracer, the first time period, the start time of the first time period, the end time of the first time period, the time frames of the scans of the subjects, the number of the scans of the subject, the bed position(s) of the PET scanner 110, or the like, or any combination thereof.

In some embodiments, the more the PET data is, the more accurate the blood input function (e.g., the first portion of the blood input function and the integral of the second portion of the blood input function) may be (as shown in FIG. 7). Because the tracer decays over time, a start time of the first time period closer to the balance time point of the tracer may lead to more and richer PET data within the same scan time (e.g., the same first time period).

In 520, the data acquisition module 420 may obtain PET data generated by the PET scanner 110 based on the scans of the subject.

The generated PET data may relate to a plurality of coincidences detected by the detector 118 in FIG. 1 during the scans of the subject. For example, the PET data may include a total number or count of photon pairs detected by each detector pair in the detector 118 of the PET scanner 110, position information related to occurrence of the plurality of coincidences along the LORs, time information (e.g., an arrival time at the detector 118 for each photon pair, and/or an occurrence time for each photon pair) of the plurality of coincidences, or the like, or any combination thereof. In some embodiments, the PET data may be in the form of list-mode data. In some embodiments, the PET data may be in the form of sinogram data. For example, the list-mode data may be projected to the sinogram data. In some embodiments, the PET data may be stored in a storage medium (e.g., the storage device 150 and/or the storage 220 of the processing device 140) of the PET system 100. The data acquisition module 420 may retrieve the PET data from the storage medium of the PET system 100 for further processing. In some embodiments, the data acquisition module 420 may obtain the PET data from the PET scanner 110 directly for further processing.

In 530, the image reconstruction module 430 may generate PET images based on the scans of the subject by reconstructing the PET data (e.g., the list-mode data or the sinogram data). In some embodiments, the image reconstruction module 430 may reconstruct a PET image based on the PET data generated during one of the scans of the subject. For example, if the PET scanner 110 performs 30 scans of the subject, the image reconstruction module 430 may reconstruct 30 PET images each of which corresponds to one of the 30 scans of the subject.

Exemplary image reconstruction techniques may include filtered back projection (FBP), an algebraic reconstruction technology (ART), a statistical reconstruction (SR) algorithm, or the like, or any combination thereof. It should be understood by those skilled in the art that the image reconstruction technique may be varied. All such variations are within the protection scope of the present disclosure.

In 540, the input function determination module 440 may determine a first portion of a blood input function (also referred to as an arterial time-activity curve (TAC)) of the tracer in the subject based on the PET images (e.g., the dynamic PET images). The first portion of the blood input function may indicate activities (or concentrations) of the tracer during the first time period.

Merely by way of example, the input function determination module 440 may determine a same ROI or volume of interest (VOI) for each of the PET images. The ROI or VOI may include at least one artery. For each PET image, the input function determination module 440 may determine an average of pixel or voxel values related to the artery in the ROI or VOI. The input function determination module 440 may assess, based on the average, the activity (or concentration) of the tracer in the blood during the time frame of a scan corresponding to the PET image. In some embodiments, the activity (or concentration) of the tracer in the blood during a time frame of a scan may be considered constant during the time frame; the average of pixel or voxel values related to the artery in the ROI or VOI during the time frame may be considered representative of the activity (or concentration) during the time frame. In some embodiments, the activity (or concentration) of the tracer in the blood during a time frame of a scan may vary during the time frame; the average of pixel or voxel values related to the artery in the ROI or VOI during the time frame may be considered corresponding to the activity (or concentration) at a time point during the time frame, e.g., the midpoint of the time frame, and representative of the activity (or concentration) during the time frame. For example, if the PET scanner 110 performs 30 scans of the subject and the image reconstruction module 430 generates 30 PET images based on the 30 scans of the subject, the input function determination module 440 may obtain 30 activity (or concentration) values of the tracer in the blood at 30 time points within the first time period by processing the 30 PET images. It should be noted that the process for determining the activity of the tracer in the blood based on a PET image is merely provided for the purposes of illustration, and not intended to limit the scope of the present disclosure. For persons having ordinary skills in the art, another relevant process may also be used to determine the activity of the tracer in the blood based on a PET image.

The input function determination module 440 may determine the first portion of the blood input function by curve fitting of the activity values of the tracer in the blood at a plurality of time points. In some embodiments, the fitting may include interpolation, extrapolation, smoothing, regression analysis, the least squares algorithm, or the like, or any combination thereof. Exemplary interpolation algorithms may include Lagrange interpolation, Newton interpolation, Hermite interpolation, piecewise interpolation, spline interpolation, linear interpolation, or the like, or a combination thereof. Exemplary extrapolation algorithms may include linear extrapolation, polynomial extrapolation, conic extrapolation, French curve extrapolation, or the like, or a combination thereof. Exemplary regression analysis may include linear regression, nonlinear regression, multiple regression, logistic regression, partial regression, or the like, or a combination thereof.

In some embodiments, the process described above for determining the first portion of the blood input function may be applicable when the PET scanner 110 performs the scans of the subject at a single bed position (or fixed field of view, FOV) during the first time period.

In some embodiments, when the PET scanner 110 performs the scans of the subject at multiple bed positions during the first time period, the input function determination module 440 may determine the first portion of the blood input function based on the PET data of the scans performed at the multiple bed positions. For example, the input function determination module 440 may determine an ROI or VOI for each of the PET images for the multiple bed positions. The ROI or VOI may include at least one artery. The ROIs or VOIs related to a same bed position may be same or at least partially overlap. The input function determination module 440 may determine an activity of the tracer for each of the PET images based on a process similar to that described above. The input function determination module 440 may modify the activity of each of the PET images based on the size of the artery in the respective ROI or VOI. Alternatively, the artery in the ROI or VOI in one of the PET images may be chosen as the standard and the input function determination module 440 may perform the modification of the rest of activities based on the standard artery size. The modification of the activities may be done by correction technologies including, e.g., partial volume effect (PVE) correction. The input function determination module 440 may combine the modified activities (and the unmodified, standard activity) to generate the first portion of the blood input function. For example, the input function determination module 440 may stitch together the modified activities (and the unmodified, standard activity) in a chronological order to generate the first portion of the blood input function. More descriptions regarding the embodiments with respect to multiple bed positions may be found in, e.g., U.S. Pat. No. 8,831,323 B2, the contents of which are hereby incorporated by reference.

In 550, the integral determination module 450 may determine an integral of a second portion of the blood input function based on a kinetic model, the PET data, and the first portion of the blood input function. The second portion of the blood input function may correspond to a second time period between the injection time and the start time of the first time period. For example, the second time period may be from the injection time to the start time of the first time period or a portion thereof.

As used in the present disclosure, the kinetic model may be a two-compartment model. In the two-compartment model, one of the two compartments may represent blood, and the other one of the two compartments may represent tissue.

In some embodiments, the integral determination module 450 may determine a Patlak estimation based on the two-compartment model for irreversible tracers. The Patlak estimation may represent a dynamic behavior of the irreversible tracers through transfer between the two compartments. The Patlak estimation may represent a relationship between the activity (or concentration) of the tracer (e.g., the irreversible tracer) in tissue and the activity (or concentration) of the tracer in blood. When the distribution of the tracer in the subject reaches the steady state, the Patlak plot may become linear. The slope of the linear phase of the Patlak plot may indicates the net transfer rate between the two compartments (e.g., tissue and blood). The intercept of the linear phase of the Patlak plot may represent the distribution volume of the tracer in the compartment of blood.

In some embodiments, the Patlak plot may be applicable to pixels or voxels of the PET images. In this case, a slope parameter (also referred to as slope value) and an intercept parameter (also referred to as intercept value) related to at least one pixel or voxel of the PET images (e.g., the pixels or voxels in the ROI or VOI of the PET images) may be determined. The kinetic parameters may include the slope parameters and the intercept parameters of the at least one voxel or pixel of the PET images.

In some embodiments, the Patlak estimation may represent a relationship of the blood input function, the PET data, and the kinetic parameters. For example, the Patlak estimation may be represented by Equation (1) as below:

$$\int_{t(l)}^{t(l)+\Delta t} y_i(t)dt = \Sigma_j P_{ij}(K_j \int_{t(l)}^{t(l)+\Delta t}(\int_0^t \text{bld}(\tau)d\tau)dt + q_j \int_{t(l)}^{t(l)+\Delta t} \text{bld}(t)dt) + \int_{t(l)}^{t(l)+\Delta t}[r_i(t)+s_i(t)]dt, \ t > T_0 \quad (1),$$

where $y_i(t)$ denotes a count of photon pairs generated at LOR i at time t; t(l) denotes a start time of time frame l; $\Delta t$ denotes a duration of time frame l; $P_{ij}$ denotes a response matrix including a plurality of elements, and each element represents a probability of a photon pair being detected by a detector pair that is connected by LOR i when the photon pair is generated at a location corresponding to voxel (or pixel) j of an PET image associated with time frame l; $K_j$ and $q_j$ are the Patlak parameters, in which $K_j$ denotes a slope value of the linear phase of the Patlak plot for voxel (or pixel) j, and $q_j$ denotes an intercept value of the linear phase of the Patlak plot for voxel (or pixel) j; bld($\tau$) and/or bld(t) denote an activity (or concentration) of the tracer at a certain time point (e.g., t or $\tau$) in the blood input function; $r_i(t)$ and $s_i(t)$ denote the random coincidence rate and the scattered coincidence rate along LOR i at time t, respectively; and $T_0$ denotes the start time of the first time period. In some embodiments, the $y_i(t)$, $P_{ij}$, $r_i(t)$, and $s_i(t)$ may be determined based on the PET data.

As illustrated in Equation (1), Equation (1) may be associated with one LOR. In order to make the Patlak estimation associated with all LORs related to the detector 118, Equation (1) may be transformed to Equation (2) as below:

$$\Sigma_i \int_{t(l)}^{t(l)+\Delta t}\{y_i(t)-[r_i(t)+s_i(t)]\}dt = \Sigma_i \Sigma_j P_{ij}(K_j \int_{t(l)}^{t(l)+\Delta t}(\int_0^t \text{bld}(\tau)d\tau)dt + q_j \int_{t(l)}^{t(l)+\Delta t} \text{bld}(t)dt), \ t > T_0 \quad (2),$$

Equation (2) may be further transformed to Equation (3) as below:

$$\Sigma_i \int_{t(l)}^{t(l)+\Delta t}\{y_i(t)-[r_i(t)+s_i(t)]\}dt = \Sigma_i \Sigma_j P_{ij}(K_j \int_{t(l)}^{t(l)+\Delta t}(\int_0^{T_0} \text{bld}(\tau)d\tau + \int_{T_0}^{t} \text{bld}(\tau)d\tau)dt + q_j \int_{t(l)}^{t(l)+\Delta t} \text{bld}(t)dt), \ t > T_0 \quad (3),$$

where $\int_0^{T_0} \text{bld}(\tau)d\tau$ denotes an integral of the second portion of the blood input function.

From Equation (3), if the PET scanner 110 starts to perform scans of the subject after the distribution of the tracer is deemed to have reached the steady state, information that need to be input to the Patlak estimation to estimate the kinetic parameters may include at least one of the integral of the blood input function corresponding to the second time period between the injection time and the start time of the first time period (e.g., the integral of the second portion of the blood input function), instead of the curve of the blood input function corresponding to the second time period, or the curve of the blood input function corresponding to the first time period. Equation (3) may provide the theoretical basis for scanning the subject after the distribution of the tracer reaches the steady state instead of from the injection time.

In some embodiments, let $$Y(l) = \Sigma_i \int_{t(l)}^{t(l)+\Delta t}\{y_i(t)-[r_i(t)+s_i(t)]\}dt \quad (4),$$

$$C = \int_0^{T_0} \text{bld}(\tau)d\tau \quad (5),$$

$$B1(l) = \int_{t(l)}^{t(l)+\Delta t}(\int_{T_0}^{t} \text{bld}(\tau)d\tau)dt \quad (6),$$

$$B2(l) = \int_{t(l)}^{t(l)+\Delta t} \text{bld}(t)dt \quad (7),$$

$$PK = \Sigma_j \Sigma_i P_{ij} K_j \quad (8), \text{ and}$$

$$Pq = \Sigma_j \Sigma_i P_{ij} q_j \quad (9).$$

Equation (3) may be transformed to Equation (10) as below based on Equations (4)-(9):

$$Y(l) = [C\Delta t + B1(l)] + PqB2(l), \ t > T_0 \quad (10),$$

where Y(l) may represent the PET data that is generated during time frame l excluding the data related to the random coincidences and the scattered coincidences.

If the PET scanner 110 performs n scans of the subject, Equation (10) may be further transformed to a matrix equation (e.g., Equation (11)) as below:

$$\begin{pmatrix} Y(1) \\ . \\ . \\ . \\ Y(n) \end{pmatrix} = \begin{pmatrix} B1(1)+C\Delta t & B2(1) \\ . & . \\ . & . \\ . & . \\ B1(n)+C\Delta t & B2(n) \end{pmatrix} \begin{pmatrix} PK \\ Pq \end{pmatrix}, \ t > T_0. \quad (11)$$

In some embodiments, the integral determination module 450 may determine a target function based on the Patlak estimation (e.g., Equation (11)), and determine the integral of the second portion of the blood input function by solving the target function. In some embodiments, the target function may represent a relationship of the PET data generated during the first time period, the first portion of the blood input function, and the integral of the second portion of the blood input function.

In some embodiments, different algorithms for determining the integral of the second portion of the blood input function may correspond to different target functions. For example, the integral determination module 450 may determine the integral of the second portion of the blood input function using a least squares (LS) algorithm. Assuming that the noise distribution of the PET data conforms with the Gaussian noise model, the integral determination module 450 may determine a target function expressed by Equation (12) as below:

$$\tilde{C} = \min_C |Y - (B+K)((B+K)^T(B+K))^{-1}(B+K)^T Y|^2, \quad (12)$$

$$t > T_0,$$

where $\tilde{C}$ represents a target function value, $$Y = \begin{pmatrix} Y(1) \\ \cdot \\ \cdot \\ \cdot \\ \cdot \\ Y(n) \end{pmatrix}, B = \begin{pmatrix} B1(1) & B2(1) \\ \cdot & \cdot \\ \cdot & \cdot \\ \cdot & \cdot \\ \cdot & \cdot \\ B1(n) & B2(n) \end{pmatrix}, \text{ and } K = \begin{pmatrix} C\Delta t & 0 \\ \cdot & \cdot \\ \cdot & \cdot \\ \cdot & \cdot \\ \cdot & \cdot \\ C\Delta t & 0 \end{pmatrix}.$$

It should be noted that the LS algorithm is merely provided for the purposes of illustration, and not intended to limit the scope of the present disclosure. For persons having ordinary skills in the art, other relevant algorithms may also be used to determine the integral of the second portion of the blood input function, for example, an expectation maximization (EM) algorithm.

In 560, the kinetic parameters determination module 460 may determine kinetic parameters of the kinetic model based on the PET data, the first portion of blood input function, and the integral of the second portion of the blood input function. For example, the kinetic parameters determination module 460 may apply the PET data, the first portion of the blood input function, and the second portion of the blood input function into the kinetic model (e.g., the Patlak estimation represented by Equation (1), Equation (2), Equation (3), Equation (10), or Equation (11)) and determine the kinetic parameters $K_j$ and $q_j$. It should be noted that there is no limitation on approaches for determining the kinetic parameter of the Patlak estimation, and any relevant approach may be used in the present disclosure.

In some embodiments, the kinetic parameter determination module 460 may reconstruct a Patlak slope image based on $K_j$ and reconstruct a Patlak intercept image based on $q_j$.

In 570, the diagnosis module 470 may determine whether there is a lesion in the subject (e.g., the ROI of the subject) based on the kinetic parameters. Merely by way of example, the diagnosis module 470 may determine whether there is a lesion in the subject and the lesion location by comparing the Patlak slope $K_j$ and the Patlak intercept $q_j$ to normal Patlak slope values and normal Patlak intercept values. In some embodiments, the normal Patlak slope values and the normal Patlak intercept values may be determined based on clinical experiments and/or empirical data. The normal Patlak slope values and the normal Patlak intercept values may be stored in a storage medium (e.g., the storage device 150 and/or the storage 220) of the PET system 100. In some embodiments, the diagnosis module 470 may output a diagnosis report indicating whether there is a lesion in the subject and the lesion location through, for example, the I/O 230 of the processing device 140 and/or the I/O 350 of the terminal 130.

Alternatively, the kinetic parameter determination module 460 may output the kinetic parameters (or the Patlak slope image and the Patlak intercept image) through, for example, the I/O 230 of the processing device 140 and/or the I/O 350 of the terminal 130. A user of the PET system 100 may make a diagnosis based on the kinetic parameters. In this case, operation 570 may be omitted.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
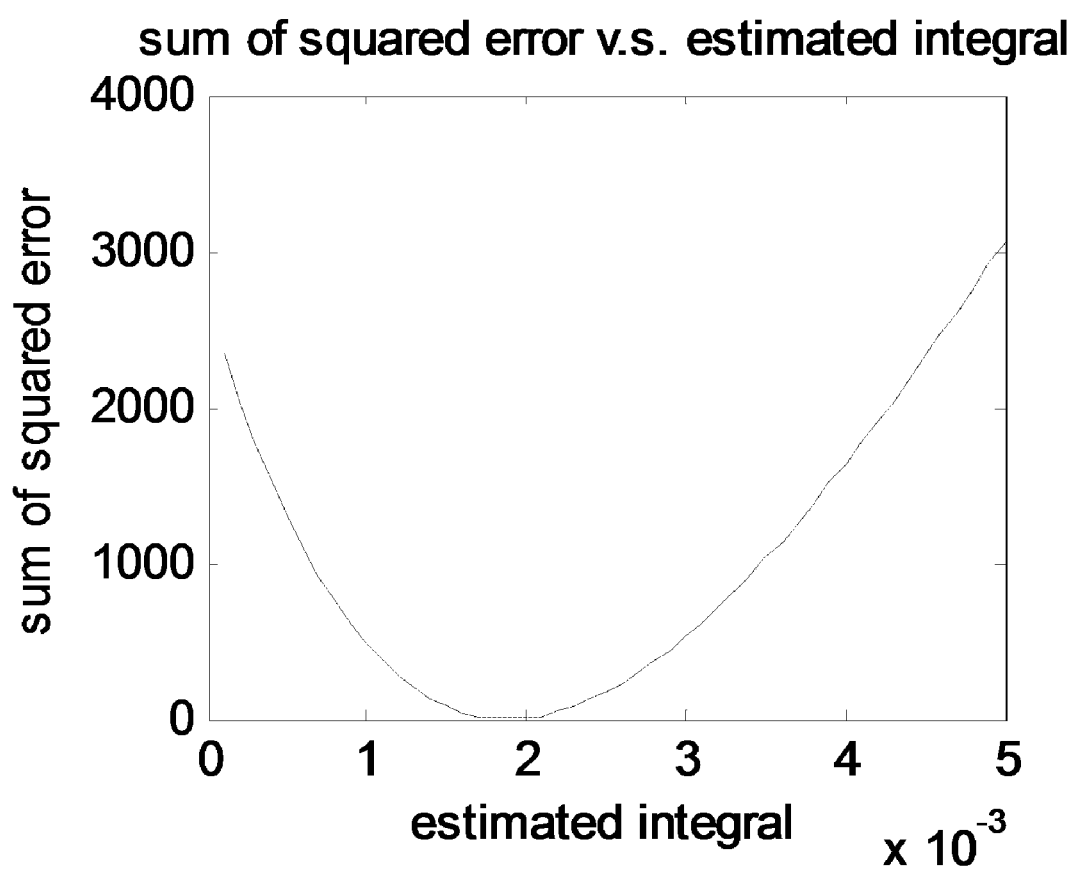
FIG. 6 is a schematic diagram illustrating an example that represents an accuracy of an estimated integral of a blood input function according to some embodiments of the present disclosure.

FIG. 6 is a schematic diagram illustrating an example that represents an accuracy of an estimated integral of a blood input function according to some embodiments of the present disclosure. As shown in FIG. 6, the horizontal axis denotes the integral of the second portion of the blood input function estimated based on the process 500 in FIG. 5. The vertical axis denotes the sum of squared errors (SSE) of the ground truth of $\int_{t(I)}^{t(I)+\Delta t} y_i(t)dt$ and the estimated value of $\int_{t(I)}^{t(I)+\Delta t} y_i(t)dt$. The ground truth of $\int_{t(I)}^{t(I)+\Delta t} y_i(t)dt$ may be determined based on the PET data. The estimated value of $\int_{t(I)}^{t(I)+\Delta t} y_i(t)dt$ may be determined by putting the estimated integral in Equation (1). In some embodiments, the integral determination module 450 may repeat operation 550 for several times and obtain a plurality of different estimated integrals because of, e.g., system errors. System errors may arise from calculation errors existing in the processing device 140, etc. As shown in FIG. 6, the minimal value of the SSE occurred at x=0.002, which means the estimated value of $\int_{t(I)}^{t(I)+\Delta t} y_i(t)dt$ is closest to the ground truth of $\int_{t(I)}^{t(I)+\Delta t} y_i(t)dt$ when the estimated integral is equal to 0.002. The kinetic parameter determination module 460 may use 0.002 to determine the kinetic parameters. It should be understood that FIG. 6 may represent the accuracy of the estimated integral.

FIG. 7 is a schematic diagram illustrating an example that represents the relative standard deviation of an estimated integral of a blood input function versus different count levels for time frames of PET scans according to some embodiments of the present disclosure. As shown in FIG. 7, the vertical axis denotes the relative standard deviation (relative s.d.) of an estimated integral of a blood input function, and the horizontal axis denotes the PET data volume (e.g., total counts of photon pairs detected by the detector 118 during each time frame of a PET scan). FIG. 7 suggests that the more the PET data is, the smaller the relative standard deviations may be. In other words, more PET data for each time frame may lead to a more accurate estimation of the integral.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for imaging, comprising:
   a positron emission tomography (PET) scanner configured to perform scans of a subject injected with a tracer during a first time period, the tracer being injected into the subject at an injection time prior to the first time period; and generate PET data based on the scans of the subject;

at least one storage device including a set of instructions; and at least one processor in communication with the at least one storage device, wherein when executing the set of instructions, the at least one processor is directed to:

generate PET images based on the scans of the subject by reconstructing the PET data;

determine a first portion of a blood input function of the tracer in the subject based on the PET images, the first portion of the blood input function corresponding to the first time period;

determine, without determining a curve of a second portion of the blood input function, an integral of the second portion of the blood input function based on a kinetic model, the PET data, and the first portion of the blood input function, the second portion of the blood input function corresponding to a second time period from the injection time to a start time of the first time period; and determine kinetic parameters of the kinetic model based on the PET data, the first portion of the blood input function, and the integral of the second portion of the blood input function, the kinetic parameters indicating a metabolism of the tracer in the subject.

2. The system of claim 1, wherein when executing the set of instructions, the at least one processor is directed to:

determine whether there is a lesion in the subject based on the kinetic parameters.

3. The system of claim 1, wherein to determine, without determining the curve of the second portion of the blood input function, the integral of the second portion of the blood input function based on the kinetic model, the PET data, and the first portion of the blood input function, the at least one processor is directed to:

determine a Patlak estimation based on the kinetic model;

determine a target function based on the Patlak estimation, the target function representing a relationship among the PET data generated during the first time period, the first portion of the blood input function, and the integral of the second portion of the blood input function; and determine, without determining the curve of the second portion of the blood input function, the integral of the second portion of the blood input function based on the target function.

4. The system of claim 3, wherein the integral of the second portion of the blood input function is determined based on a least squares (LS) algorithm.

5. The system of claim 3, wherein the integral of the second portion of the blood input function is determined based on an expectation maximization (EM) algorithm.

6. The system of claim 1, wherein the tracer is applicable to a two-tissue compartment model.

7. The system of claim 1, wherein the tracer is an irreversible tracer.

8. The system of claim 1, wherein the start time of the first time period is equal to a time point at which the distribution of the tracer in the subject is deemed to have reached a steady state.

9. The system of claim 1, wherein the start time of the first time period is after a time point at which the distribution of the tracer in the subject is deemed to have reached a steady state.

10. The system of claim 1, wherein the PET scanner performs the scans of the subject at a single bed position or at multiple bed positions.

11. A method for imaging implemented on a computing device having one or more processors and one or more storage devices, the method comprising:

directing a positron emission tomography (PET) scanner to perform scans of a subject injected with a tracer during a first time period, the tracer being injected into the subject at an injection time prior to the first time period;

generating PET images by reconstructing the PET data that are generated by the PET scanner based on the scans of the subject;

determining a first portion of a blood input function of the tracer in the subject based on the PET images, the first portion of the blood input function corresponding to the first time period;

determining, without determining a curve of a second portion of the blood input function, an integral of the second portion of the blood input function based on a kinetic model, the PET data, and the first portion of the blood input function, the second portion of the blood input function corresponding to a second time period from the injection time to a start time of the first time period; and determining kinetic parameters of the kinetic model based on the PET data, the first portion of the blood input function, and the integral of the second portion of the blood input function, the kinetic parameters indicating a metabolism of the tracer in the subject.

12. The method of claim 11, the method further comprising:

determining whether there is a lesion in the subject based on the kinetic parameters.

13. The method of claim 11, wherein the determining of, without determining the curve of the second portion of the blood input function, the integral of the second portion of the blood input function based on the kinetic model, the PET data, and the first portion of the blood input function includes:

determining a Patlak estimation based on the kinetic model;

determining a target function based on the Patlak estimation, the target function representing a relationship among the PET data generated during the first time period, the first portion of the blood input function, and the integral of the second portion of the blood input function; and determining, without determining the curve of the second portion of the blood input function, the integral of the second portion of the blood input function based on the target function.

14. The method of claim 13, wherein the integral of the second portion of the blood input function is determined based on a least squares (LS) algorithm.

15. The method of claim 13, wherein the integral of the second portion of the blood input function is determined based on an expectation maximization (EM) algorithm.

16. The method of claim 11, wherein the tracer is applicable to a two-tissue compartment model.

17. The method of claim 11, wherein the tracer is an irreversible tracer.

18. The method of claim 11, wherein the start time of the first time period is equal to or after a time point at which the distribution of the tracer in the subject is deemed to have reached a steady state.

19. The method of claim 11, wherein the PET scanner performs the scans of the subject at a single bed position or at multiple bed positions.

20. A non-transitory computer readable medium on which are stored instructions that, when executed, cause a programmable device to direct a positron emission tomography (PET) scanner to perform scans of a subject injected with a tracer during a first time period, the tracer being injected into the subject at an injection time prior to the first time period;

generate PET images by reconstructing the PET data that are generated by the PET scanner based on the scans of the subject;

determine a first portion of a blood input function of the tracer in the subject based on the PET images, the first portion of the blood input function corresponding to the first time period;

determine, without determining a curve of a second portion of the blood input function, an integral of the second portion of the blood input function based on a kinetic model, the PET data, and the first portion of the blood input function, the second portion of the blood input function corresponding to a second time period from the injection time to a start time of the first time period; and determine kinetic parameters of the kinetic model based on the PET data, the first portion of the blood input function, and the integral of the second portion of the blood input function, the kinetic parameters indicating a metabolism of the tracer in the subject.

* * * * *